US011317246B1

(12) United States Patent
Pipher et al.

(10) Patent No.: US 11,317,246 B1
(45) Date of Patent: Apr. 26, 2022

(54) FLEXIBLE MESH NETWORK FOR LOCATING ASSETS IN A CLINICAL ENVIRONMENT

(71) Applicant: Hill-Rom Services, Inc., Batesville, IN (US)

(72) Inventors: Britten J. Pipher, Fuquay-Varina, NC (US); Kenzi L. Mudge, Raleigh, NC (US); Frederick Collin Davidson, Apex, NC (US)

(73) Assignee: Hill-Rom Services, Inc., Batesville, IN (US)

(*) Notice: Subject to any disclaimer, the term of this patent is extended or adjusted under 35 U.S.C. 154(b) by 57 days.

(21) Appl. No.: 17/003,890

(22) Filed: Aug. 26, 2020

Related U.S. Application Data

(60) Provisional application No. 62/892,384, filed on Aug. 27, 2019.

(51) Int. Cl.
| | |
|---|---|
| *H04W 4/029* | (2018.01) |
| *H04W 84/20* | (2009.01) |
| *G06K 19/07* | (2006.01) |
| *G16H 40/20* | (2018.01) |
| *H04W 12/088* | (2021.01) |

(52) U.S. Cl.
CPC ........ *H04W 4/029* (2018.02); *G06K 19/0723* (2013.01); *G16H 40/20* (2018.01); *H04W 12/088* (2021.01); *H04W 84/20* (2013.01)

(58) Field of Classification Search
CPC .............. G06K 19/0723; G16H 40/20; H04M 2242/30; H04W 4/02–029; H04W 12/088; H04W 12/63; H04W 64/00–006; H04W 84/20
See application file for complete search history.

(56) References Cited

U.S. PATENT DOCUMENTS

| | | |
|---|---|---|
| 6,580,393 B2 | 6/2003 | Holt |
| 7,899,006 B2 | 3/2011 | Boyd |
| 8,031,120 B2* | 10/2011 | Smith .................. H04W 4/029 342/451 |

(Continued)

OTHER PUBLICATIONS

"Asset Tracking System in Real Time," Litum, retrieved from <<https://litum.com/our-solutions/real-time-asset-tracking>> on Aug. 26, 2020, available as early as Apr. 11, 2019, 5 pages.

(Continued)

*Primary Examiner* — Ronald Eisner
(74) *Attorney, Agent, or Firm* — Lee & Hayes, P.C.

(57) ABSTRACT

An example system connects to a location engine in a mesh network, transmits a first message indicating a bus master service hosted by a bus master, and receives a message indicating a location service hosted by a location engine and an aggregation service hosted by an aggregator connected to the location engine. The bus master stores a first entry corresponding to the location service and a second entry corresponding to the aggregation service. The bus master transmits a request to access the location service; receives a response confirming a subscription to the location service; and receives timing data indicating times at which the multiple receivers in a clinical environment received a wireless signal from a tag. The bus master aggregates the timing data into a data stream and transmits data stream to the location service in accordance with the subscription.

16 Claims, 11 Drawing Sheets

(56) References Cited

U.S. PATENT DOCUMENTS

| | | | |
|---|---|---|---|
| 8,838,481 | B2 | 9/2014 | Moshfeghi |
| 9,513,370 | B2 | 12/2016 | Cristache |
| 9,571,143 | B2 | 2/2017 | Richley |
| 9,641,964 | B2 | 5/2017 | Kulkarni et al. |
| 9,860,688 | B2 | 1/2018 | Kulkarni et al. |
| 9,866,507 | B2 | 1/2018 | Frenkel et al. |
| 2003/0039248 | A1 | 2/2003 | Weaver |
| 2008/0094228 | A1 | 4/2008 | Welch et al. |
| 2011/0211563 | A1 | 9/2011 | Herrala et al. |
| 2013/0254304 | A1 | 9/2013 | Van Nest et al. |
| 2013/0285794 | A1 | 10/2013 | Hansen |
| 2014/0361875 | A1 | 12/2014 | O'Hagan et al. |
| 2016/0117915 | A1 | 4/2016 | Llewellyn, Jr. |
| 2020/0389869 | A1* | 12/2020 | Patil ................... H04W 40/22 |

OTHER PUBLICATIONS

"Cisco Kinetic Edge & Fog Processing Module," Cisco, retrieved from <<https://www.cisco.com/c/dam/en/us/solutions/collateral/internet-of-things/cisco-kinetic-efm-whitepaper.pdf>> on Apr. 11, 2019, published Mar. 31, 2018, 26 pages.

Costin, A. et al., "Fusing Passive RFID and BIM for Increased Accuracy in Indoor Localization," Visualization in Engineering, 3:17, Dec. 2015, 20 pages.

D'Souza, M., et al., "Evaluation of Realtime People Tracking for Indoor Environments Using Ubiquitous Motion Sensor and Limited Wireless Network Infrastructure," Pervasive and Mobile Computing, vol. 9, Issue 4, Aug. 2013, Abstract, 2 pages.

D'Souza, M. et al., "Indoor Position Tracking Using Received Signal Strength-based Fingerprint Context Aware Partitioning," IET Radar, Sonar and Navigation, vol. 10, Issue 8, Oct. 2016, 18 pages.

"Function Description—Location in Ascom VoWiFi System," TD92607GB, retrieved from <<http://www.ascomwireless.com/pdf/guide/vowifi/location_vowifi_fd_92607gb.pdf>> on Apr. 15, 2019, published Dec. 13, 2010, 11 pages.

Kwan, Dennis, "Bluetooth Mesh Profile Applied to RTLS," Bluetooth Blog, retrieved from <<https://blog.bluetooth.com/bluetooth-mesh-profile-applied-to-rtls>> on Apr. 11, 2019, published Oct. 30, 2017, 5 pages.

Miekk-oja, V., "Static Beacons Based Indoor Positioning Method for Improving Room-level Accuracy," Aalto University School of Electrical Engineering, Apr. 28, 2015, 87 pages.

Najib, et al., "A Software Development Model for Localization Systems," retrieved from <<https://www.researchgate.net/publication/228343991_A_Software_Development_Model_for_Localization_Systems>> on Apr. 15, 2019, published May 2009, 6 pages.

"High-Precision RTLS," Redpoint Positioning, retrieved from <<https://www.redpointpositioning.com/wp-content/uploads/2015/06/RedpointSolutionsBrochure.pdf>> on Apr. 11, 2019, published Jun. 27, 2015, 4 pages.

Schmitt, S., et al., "The Effects of Human Body Shadowing in RF-based Indoor Localization," 2014 International Conference on Indoor Positioning and Indoor Navigation, Oct. 2014, 8 pages.

Trogh J., et al., "Enhanced Indoor Location Tracking Through Body Shadowing Compensation," Department of Information Technology, iMinds—Ghent University, Dec. 2015, 9 pages.

\* cited by examiner

FLEXIBLE MESH NETWORK FOR LOCATING ASSETS IN A CLINICAL ENVIRONMENT

CROSS-REFERENCE TO RELATED APPLICATION

This application claims the benefit of U.S. Application No. 62/892,384, which was filed on Aug. 27, 2019, and which is incorporated by reference herein in its entirety.

TECHNICAL FIELD

This application relates generally to a Real Time Locating System (RTLS) configured to track the locations of assets in a clinical environment. The RTLS can include a mesh network with multiple nodes that can provide services to other nodes in the network.

BACKGROUND

Hospitals, and other types of healthcare environments, track a variety of different assets, and determining/monitoring the locations of such assets can be important when administering care to patients. For instance, the positions of medical devices, hospital beds, and other clinically-relevant objects may be relevant to providing and maintaining a high level of care in these environments. In various examples, the positions of patients may be significant for managing their care. In various cases, the positions of care providers (e.g., nurses, physicians, and the like) may also be important for efficiently delivering care in the clinical environment. Tracking the positions of these and other clinically-relevant assets in real time can enable centralized systems (e.g., nurse call systems) within the clinical environment to efficiently deploy resources to care for the patients in the clinical environment.

An RTLS can be used to track the locations of objects and people in various settings. In the RTLS, a tag may emit a wireless signal that can be received by multiple receivers. Based on the times-of-flights (or angles-of-arrival) of the wireless signal being received by the multiple receivers, and the positions of the receivers, a tag's location can be derived within an environment.

However, broad adoption of RTLS in healthcare settings to track objects, patients, and care providers is not without challenges. There is a need for more accurate RTLS technologies adapted for various healthcare environments. In addition, due to significant variances between various healthcare environments, there is a need for a flexible RTLS platform that can be adapted for various clinical settings.

SUMMARY

Various implementations of the present disclosure relate to a flexible mesh network to support a location system, such as an RTLS. The mesh network can be used to identify the locations of assets in a clinical environment.

In various implementations, a first network node (e.g., a bus master, locating engine, aggregator, or some other network node that may or may not be actively hosting a service) can join an existing network by connecting to a second network node (e.g., a bus master, locating engine, or aggregator). Once a connection is established, the first network node and the second network node can exchange information about services hosted by the individual nodes, as well as service hosted by other nodes connected to the first and second nodes. Each node may update a local service list based on the exchange of information. The service list can include a list of the services provided by the network, routing information related to accessing the services, and the like.

The first node can use its local service node to determine whether to subscribe to a particular service hosted by the second node, or by another node in the network connected to the second node. In response to determining to subscribe to a service, the first node can transmit a request for the service to the second node. If the service is provided by the second node, then the second node can establish a subscription to the service directly. If the service is not provided to the second node, then the second node can forward the request to an appropriate node in the network based on information in the request and/or information stored in its own service list. In some cases, the second node can route data associated with a subscribed service between the first node and the other node offering the service.

If the first node leaves the network, the second node can update other nodes in the network about the first node leaving the network. For instance, upon identifying that the first node has left the network, the second node may transmit service list updates to the other nodes indicating that the service provided by the first node is no longer available. In response to receiving a service update indicating that a service is no longer available, a node may use its own service list to identify and subscribe to another, similar service within the network.

Various implementations of the present disclosure provide improvements to the field of RTLS, particularly as applied to clinical environments. Unlike previous technologies, implementations of the present disclosure can be used to establish peer-to-peer connections between various nodes in a network, rather than relying on the unidirectional client-service mode. Various flexible networks described herein can allow arbitrary roles to be assumed in connections between various nodes in the network. Because clinical environments can have diverse orientations and needs, implementations that allow connections between nodes in different directions of the network can be particularly helpful for providing customized RTLS networks in clinical environments. In addition, various clinical environments may have needs that change over time. Implementations of the present disclosure enable a flexible network size and topology that can be easily customized based on the immediate needs of the applicable clinical environment. Further, various implementations of the present disclosure provide more robust RTLS networks. In some example implementations, nodes can easily identify interruptions within the network and re-subscribe to alternative services in order to maintain high functionality despite those interruptions.

Furthermore, various implementations of the present disclosure can enable communication between nodes that are separated by firewalls. For instance, in certain healthcare environments, firewalls are utilized between network nodes to protect confidential patient information and/or to comply with various regulatory requirements. In some networks, a first node hosting a service may be separated from a second node by a firewall, and a third node seeking to access the first node may be connected to the second node, such that the second node is present between the firewall and the third node. However, the firewall may prevent the third node from accessing the service hosted by the first node. In various implementations described herein, however, the third node can access the service hosted by the first node via the second node. Accordingly, a functional mesh topology can be applied to a broad array of healthcare environments.

DESCRIPTION OF THE FIGURES

The following figures, which form a part of this disclosure, are illustrative of described technology and are not meant to limit the scope of the claims in any manner.

DETAILED DESCRIPTION

Figure 1:
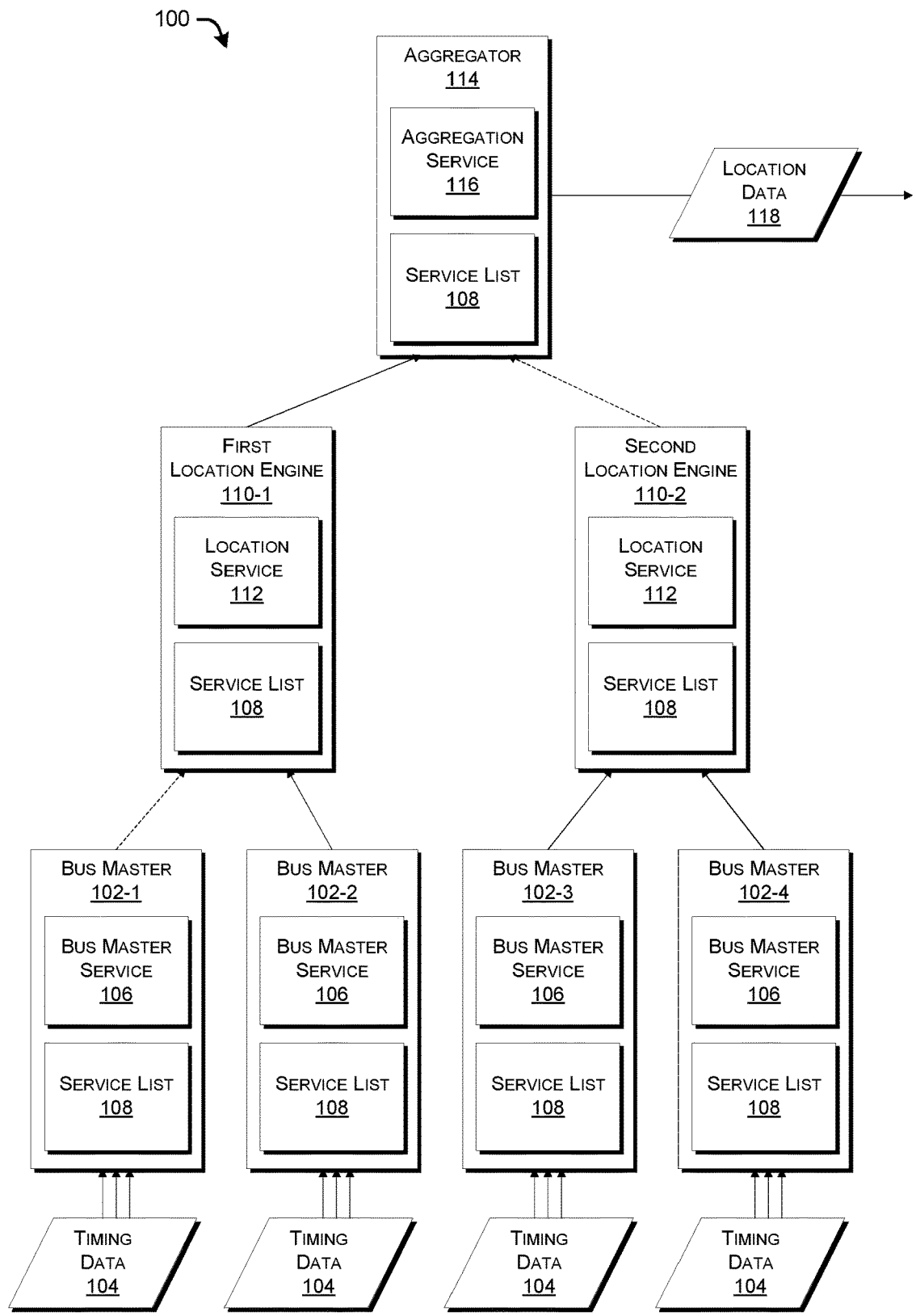
FIG. 1 illustrates an example environment including a flexible mesh network within a location system.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

FIG. 1 illustrates an example environment 100 including a flexible mesh network within a location system, such as an RTLS. As illustrated, the environment 100 includes multiple bus masters 102-1 to 102-4, which may be referred to singularly as "bus master 102" or plurally as "bus masters 102."

Each of the bus masters 102 may receive multiple streams of timing data 104 indicating times at which multiple receivers in a clinical environment receive wireless signals from tags. As used herein, the term "tag" can refer to a physical device capable of storing information, transmitting information to a remote device, and/or receiving information from a remote device. A tag may be attached to a physical object (e.g., a medical device, a hospital bed, or the like). In various implementations, a tag can be passive, such that it collects energy from outside sources (e.g., radio waves) to power storage, data transmission, processing, or the like. In some implementations, a tag can be active, such that it may include a power source that can be used to power storage, data transmission, processing, or the like. Some examples of tags include Radio-Frequency Identification (RFID) tags, which can use electromagnetic signals to communicate with external devices. However, some tags can use non-radio-frequency electromagnetic signals, acoustic signals, or the like, to communicate with external devices.

The tags may be attached to, held by, worn by, or otherwise associated with assets, such as objects (e.g., medical devices, hospital beds, or the like) or people (e.g., patients, care providers, or the like). In some cases in which the asset is an object (e.g., a medical device, a hospital bed, or the like), a tag may be attached to the object. In some cases in which the asset is a person (e.g., a patient, care provider, or the like), a tag may be worn by the person. In some instances, the tag may be worn on a lanyard or necklace around the person's neck. In some examples, the tag may be integrated into a wristband that is worn by the person. In some instances, the tag may be integrated into clothes worn by the person.

Using a bus master service 106 hosted by each of the bus masters 102, the bus masters 102 may aggregate the multiple data streams into a single data stream for further analysis. The bus master service 106 may be a software service, Virtual Machine (VM), independent device, or the like.

Each of the bus masters 102 may also include a service list 108. The service list 108 may be a list of various services provided by nodes in the flexible mesh network. For example, the service list 108 may identify services associated with the other nodes, routing information that enables the bus master 102 to communicate with the other nodes, and identifiers of the other nodes. Using the information stored in the service list 108, the bus masters 102 may efficiently identify and subscribe to various other services within the mesh network.

Each of the bus masters 102 may transmit the single data stream representing the timing data 104 to at one or more location engines, such as a first location engine 110-1 and a second location engine 110-2. The first and second location engines 110-1 and 110-2 may be referred to singularly as "location engine 110" or plurally as "location engines 110." Using a location service 112, each of the location engines 110 may be configured to identify, estimate, and/or calculate the locations of the tags within the clinical environment based on the single data streams forwarded by the bus masters 102. The location service 112 may be a software service, VM, independent device, or the like. Similar to the bus masters 102, the location engines 110 may also host a service list 108 that identifies services associated with other nodes in the flexible mesh network.

The location engines 110 may individually transmit data streams representing the locations of the tags to an aggregator 114. In various implementations, the flexible mesh network may have a single aggregator 114. The aggregator 114 may host an aggregation service 116 that enables the aggregator 114 to combine the data streams representing the locations calculated by the individual location engines 110 into a single data stream of location data 118. In some cases, the aggregator 114 can transmit the location data 118 to an external reporting system, which can take various actions throughout the clinical environment based on the locations of the tags.

The design of the flexible mesh network enables network nodes, such as the bus masters 102, location engines 110, and aggregator, to be easily connected. For instance, a first bus master 102-1 may connect to the first location engine 110-1. After exchanging routing information enabling the first bus master 102-1 and the first location engine 110-1 to communicate with each other (e.g., using Transmission Control Protocol (TCP)/Internet Protocol (IP)), the first bus master 102-1 may transmit a message indicating the bus master service 106 hosted by the first bus master 102-1.

Upon receiving the message from the first bus master 102-1, the first location engine 110-1 may update its service list 108 to indicate the bus master service 106 hosted by the first bus master 102-1. In addition, the first location engine 110-1 may inform other nodes in the network of the bus master service 106 hosted by the first bus master 102-1. For example, the first location engine 110-1 may transmit a message to a second bus master 102-2 and a message to the aggregator 114, both indicating the bus master service 106 hosted by the first bus master 102-1. Upon receiving the update about the new service provided by the first bus master 102-1, subsequent nodes throughout the network can update their respective service lists 108 and transmit other update messages to inform other nodes of the bus master service 106 hosted by the bus master 102-1. In addition, using the service list 108 of the first location engine 110-1, the first location engine 110-1 can transmit a message to the first bus master 102-1 indicating the services provided by other nodes that are already present in the network, such as the location service 112 hosted by the first location engine 110-1, the aggregation service 116 hosted by the aggregator, and the bus master service 106 hosted by the second bus master 102-2.

Similarly, the second location engine 110-2 may connect to the aggregator 114. After exchanging routing information enabling the second location engine 110-2 to communicate with the aggregator 114, the second location engine 110-2 may transmit a message indicating the location service 112 hosted by the second location engine 110-2. In addition, the second location engine 110-2 may already be connected to other network nodes, such as third and fourth bus masters 102-3 and 102-4, prior to connecting to the aggregator 114. By referencing its service list 108, the second location engine 110-2 may also indicate the bus master services 106 hosted by the third and fourth bus masters 102-3 and 102-4 in the message to the aggregator 114. Accordingly, the aggregator 114 can distribute information about the services hosted by the second location engine 110-2, the third bus master 102-3, and the fourth bus master 102-4, throughout the rest of the mesh network. In addition, using the service list 108 of the aggregator 114, the aggregator 114 can transmit a message to the second location engine 110-2 indicating the services provided by other nodes that are already present in the network, such as the aggregation service 116 hosted by the aggregator 114, the location service 112 hosted by the first location engine 110-1 and the bus master services 106 hosted by the first and second bus masters 102-1 and 102-2.

The flexible mesh network depicted in FIG. 1 enables nodes to efficiently subscribe to services provided throughout the network. For instance, the second location engine 110-2 may identify that the first bus master 102-1 is hosting a bus master service 106 based on the exchange of service messages with the aggregator 114. The second location engine 110-2 may determine to access (e.g., subscribe to) the bus master service 106 hosted by the first bus master 102-1. For instance, the second location engine 110-2 may execute an instruction, stored in memory, to access any bus master service 106 that becomes available in the network. In response to determining to access the bus master service 106, the second location engine 110-2 may transmit a subscription request to the first bus master 102-1 via the aggregator 114 and the first location engine 110-1. In response to the request, the first bus master 102-1 may transmit a response confirming the subscription to the second location engine 110-1 via the first location engine 110-1 and the aggregator 114. Based on routing information stored in their respective service lists, the aggregator 114 and the first location 110-1 may forward the request and the response between the second location engine 110-2 and the first bus master 102-1. Once the second location engine 110-2 is connected (e.g., subscribed) to the bus master service 106 of the first bus master 102-1, the single data stream output by the first bus master 102-1 may be forward to the second location engine 110-2 through the first location engine 110-1 and the aggregator 114. Accordingly, the second location engine 110-2 may be enabled to calculate the location of tags represented by the timing data 104 aggregated by the first bus master 102-1.

Furthermore, the flexible mesh network can be used to efficiently identify and respond to outages and disconnections of nodes within the network. When a first node identifies that a second node has disconnected from the first node, the second node may automatically update other nodes in the network that the service(s) offered by the first node are no longer available. For instance, if the first location engine 110-1 identifies that the first bus master 102-1 has been disconnected from the first location engine 110-1, the first location engine 110-1 may automatically transmit messages to the aggregator 114 and the second bus master 102-2 indicating that the bus master service 106 hosted by the first bus master 102-1 is no longer available. The aggregator 114, as well as other nodes in the network, may further distribute the update throughout the rest of the network. In addition, the first location engine 110-1, as well as the other nodes in the network, may update their respective service lists 108 to indicate that the bus master service 106 of the first bus master 102-1 is no longer available.

Figure 2:
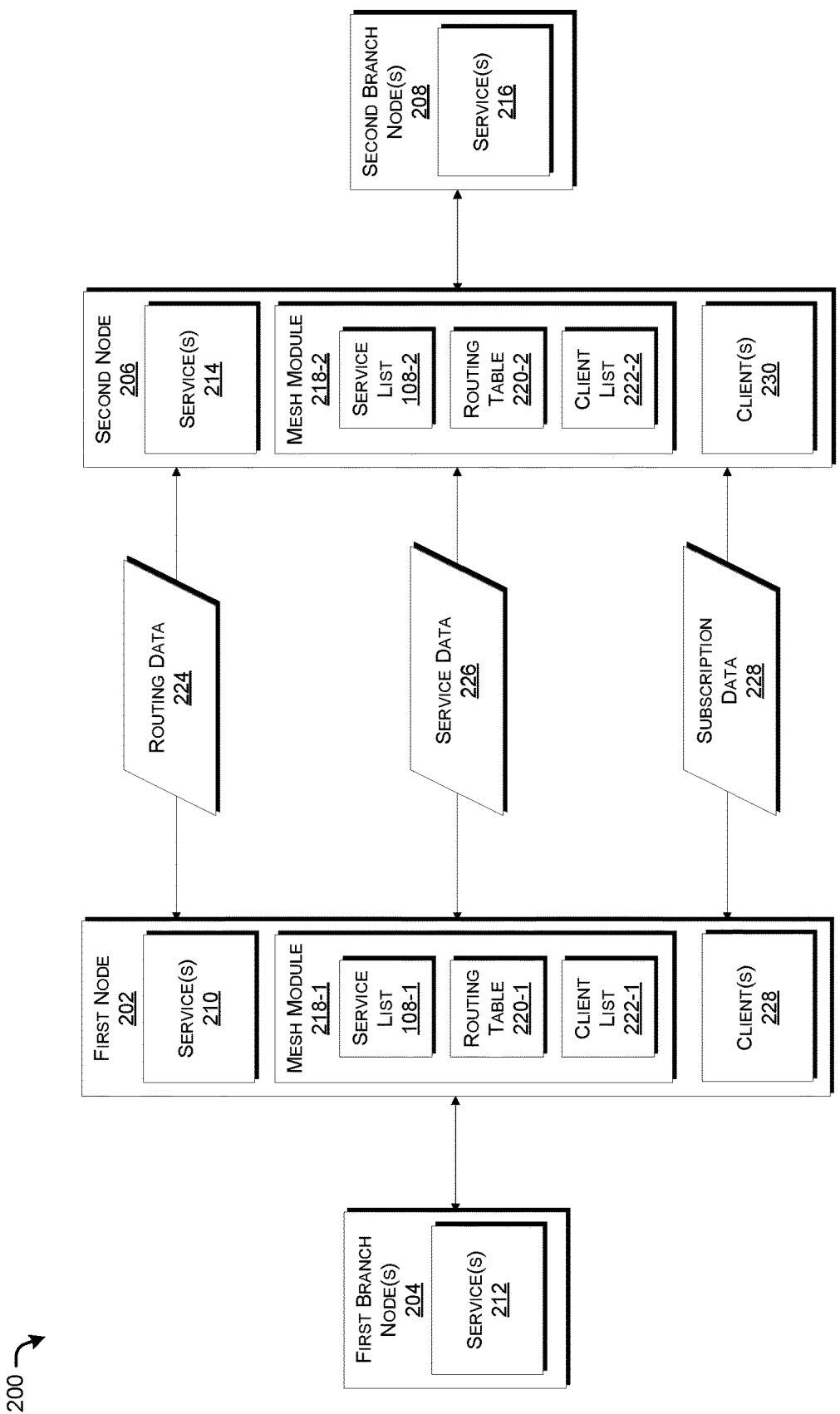
FIG. 2 illustrates a generic environment of nodes in a flexible mesh network.

FIG. 2 illustrates a generic environment 200 of nodes in a flexible mesh network. The environment includes a first node 202, one or more first branch nodes 204, a second node 206, and one or more second branch nodes 208, which may each correspond to at least one of the bus masters 102, location engines 110, or aggregator 114 described above with reference to FIG. 1. The first node 202 and the second node 206, for instance, each include a service list 108-1 or 108-2.

The first node 202 may be connected to the first branch node(s) 204. The first branch node(s) 204 may include nodes directly connected to the first node 202, as well as nodes indirectly connected to the first node 202 via one or more other nodes. The first node 202 may host one or more services 210. In addition, the first branch node(s) 204 may host one or more services 212. Similarly, the second node 206 may be connected to the second branch node(s) 208. The second branch node(s) 208 may include nodes directly connected to the second node 206, as well as nodes indirectly connected to the second node 206 via one or more other nodes. The second node 206 may host one or more services 214. In addition, the second branch node(s) 208 host one or more services 216. In some examples, the services 210, 212, 214, and 216 can be bus master services, location services, and/or aggregation services. However, implementations are not so limited. In some instances, which may or may not apply to RTLS implementations, the services 210, 212, 214, and 216 can include data publication services (e.g., services that export data for storage and/or publication), configuration services, industrial control services, test-related services (e.g., services that report and/or request testing data of the network) and the like.

The first and second nodes 202 and 206 may respectively include mesh modules 218-1 and 218-2. Each mesh module 218-1 or 218-2 may be a Virtual Machine (VM), software module, or software object configured to maintain routing information, maintain a local list of discovered services, route messages, track which clients are subscribed to which services, create virtual sockets, or the like. As illustrated, mesh module 218-1 in the first node 202 can include a service list 108-1, and mesh module 218-2 in the second node 206 can include a service list 108-2. The service list 108-1 can include a list of services throughout the mesh network, such as a list of the services 212, 214, and 216. The service list 108-2 may include a list of services that includes the services 210, 212, and 216.

The mesh modules 218-1 and 218-2 may further include routing tables 220-1 and 220-2, respectively. Each one of the routing tables 220-1 and 220-2 may be a data table that lists how data is routed to other nodes, services hosted by the other nodes, and/or clients hosted by the other nodes, within the network. For instance, the routing table 220-1 may include a list of routes from the first node 202 to any of the first branch node(s) 204, to the second node 206, and to any of the second branch node(s) 208. Similarly, the routing table 220-2 may include a list of routes from the second node 206 to any of the first branch node(s) 204, to the first node 202, and to any of the second branch node(s) 208. In some cases, each of the routing tables 220-1 and 220-2 can include at least an identifier of the destination node (or an identifier of a particular service hosted by the destination node) and a next hop (also referred to as a gateway) identifier that represents the first node along the pathway to the destination node. For instance, the routing table 220-1 may include an entry for a second branch node that includes an identifier of the second branch node 208 as well as an identifier for the second node 204, through which data destined for the second branch node 208 should be routed. In some cases, each entry may further include a cost or metric that represents a number of hops required to reach the destination node.

In some implementations, the mesh modules 218-1 and 218-2 may include client lists 222-1 and 222-2, respectively. Each one of the client lists 222-1 and 222-2 may include a list of client nodes that are subscribed to the services 210 or 214. For instance, the client list 222-1 of the first node 202 may include a list of client nodes subscribed to the services 210, and the client list 222-2 of the second node 206 may include a list of client nodes subscribed to the services 214.

The first and second nodes 202 and 206 may connect to each other via a communication interface. For instance, the first and second nodes 202 and 206 may connect to a wired Local Area Network (LAN). When the first node 202 and the second node 206 connect to each other, they may initially exchange routing data 224. The routing data 224 may include, for example, at least one of addresses of the first node 202 and the second node 206, virtual ports associated with the services 210 and 214 hosted by the first and second nodes 202 and 206, a next hop mapping data. The routing data 224 may enable the first and second nodes 202 and 206 to communicate via a particular communication protocol, such as File Transfer Protocol (FTP), an electronic trading protocol, an instant messaging protocol, or a communication protocol specific to the environment 200. In some cases, the routing data 224 may enable the first and second nodes 202 and 206 to communicate via an exchange of data in a particular format, such as ASN.1, Google Protocol Buffer, XML, JSON, or the like. In some cases, the communication protocol can be used to package data transmitted between the first and second nodes 202 and 206, such that the data packets can be forwarded by the first and second nodes 202 and 206 to appropriate destination nodes (e.g., the first branch node(s) 204 or the second branch node(s) 208) and/or services (e.g., the services 212 or 216) without the first and second nodes 202 and 206 inspecting the contents (e.g., payloads) of the data packets.

In some cases, the addresses can be one or more unique identifiers of the first node 202 and the second node 206. For instance, the addresses of the nodes can be strings, identification numbers, Domain Name Service (DNS) names, IP addresses, Media Access Control (MAC) addresses, or the like.

The virtual ports may include one or more unique (e.g., alphanumeric) identifiers of each service hosted by individual nodes. For instance, the virtual ports may be identified by service identifiers, such as the service identifiers 304 described below with reference to FIG. 3. In some cases, the virtual ports may include port numbers of each of the first and second nodes 202 and 206 that identify the service(s) 210 and the service(s) 214.

The next hop mapping data can identify the first branch node(s) 204, the service(s) 212 hosted by the first branch node(s) 204, the second branch node(s) 208, and the service(s) 216 hosted by the second branch node(s) 208. For instance, the next hop mapping data transmitted from the first node 202 to the second node 206 may include a data object that indicates identifiers of the first branch node(s) 204 and the associated services 212 hosted by the first branch node(s) 204. Accordingly, if the second node 206 was to later subscribe to a service 212 hosted by a first branch node 204, the second node 206 may transmit a request to subscribe to the service 212 to the first node 202 with an indication of the service 212 and/or the first branch node 204, thereby enabling the first node 202 to forward the request to the appropriate first branch node 204.

The first node 202 and the second node 206 may exchange service data 226. The service data 226 may include messages indicating the service(s) 210 hosted by the first node 202 and the service(s) 214 hosted by the second node 206. In addition, the service data 226 may include messages indicating the service(s) 212 hosted by the first branch node(s) 204 as well as the service(s) 216 hosted by the second branch node(s) 208. In response to receiving the messages within the exchange of service data 226, the first and second nodes 202 and 206 may update their respective service lists 108-1 or 108-2. Accordingly, the first and second nodes 202 and 206 may be aware of the services provided throughout the mesh network. After the first node 202 connects to the second node 206, the mesh network may include the first node 202, the first branch node(s) 204, the second node 206, and the second branch node(s) 208.

One or more clients 228 and 230 of the first node 202 and/or the second node 206 may determine to access (e.g., subscribe to) one of the services in the mesh network. Each one of the clients 228 and 230 can refer to a VM, software module, software object, or the like that is configured to subscribe to a service (e.g., any of the services 210, 212, 214, and 216) and receive data from that service. In some cases, the clients 228 and 230 may determine to access a service automatically. For instance, a client associated with an aggregator node may be configured to always subscribe to any available location engine. In some cases, either or both of the clients 228 and 230 may unsubscribe to any of the services on the mesh network, according to various rules implemented by the clients 228 and 230.

In various examples, the client(s) 228 may determine to access (e.g., subscribe to) the service(s) 214 hosted by the second node 206 or the service(s) 216 hosted by the second branch node(s) 208. To access the service, the client(s) 228 of the first node 202 may transmit a request to access the service to the second node 206. The request may be provided in service data 226. If the service requested by the client(s) 228 of the first node 202 is the service 214 hosted by the second node 206, the second node 206 may establish the subscription. For instance, the mesh module 218-2 of the second node 206 may provide a virtual socket (or some other socket known to those in the art) to enable communication between the service 214 and the client(s) 228. As used herein, the term "virtual socket" can refer to a software object providing virtual point of entry into a node, a client within a node, and/or service within a node. In some cases, the virtual socket may establish a bearer between nodes (e.g., at least one service and/or at least one client) through a network. A virtual socket may be associated with a virtual address, such as an IP address, a port address, and/or some other type of unique identifier for the virtual socket within the network. In some cases, data packets transmitted between virtual sockets in a network may be packaged in a protocol that is specific to the virtual sockets. For instance, data packets transmitted between virtual sockets may include payloads in a particular data representation format, such as XML, JSON, or the like. Data packets transmitted between other types of virtual sockets can be packaged differently. The packaging of the data packets can hide the contents of the data packets from intermediary nodes and sockets through which the data packets are transmitted along one or more pathways between a source (node, client, and/or service) and a destination (node, client, and/or service).

If the service requested by the first node 202 is the service 216 provided by the second branch node 208, the mesh module 218-2 of the second node 206 may refer to the routing table 220-2 and forward the request to access the service 216 to the second branch node 208, so that the second branch node 208 can establish the connection between the client(s) 228 of the first node 202 and the service 216 (e.g., a subscription to the service 216). For instance, the second branch node 208 may provide a virtual socket (or some other suitable socket) to enable communication between the service 216 and the client(s) 228 of the first node 202, wherein communications between the service 216 and the client(s) 228 may be routed automatically through the second node 206. Once the client(s) 228 of the first node 202 is connected (e.g., subscribed) to a service 214 or 216, data may be transmitted from the client(s) 228 to the service 214 or 216, or transmitted from the service 214 or 216 to the client(s) 228, in accordance with the subscription. This data may also be part of the subscription data 222, in various implementations.

Figure 3:
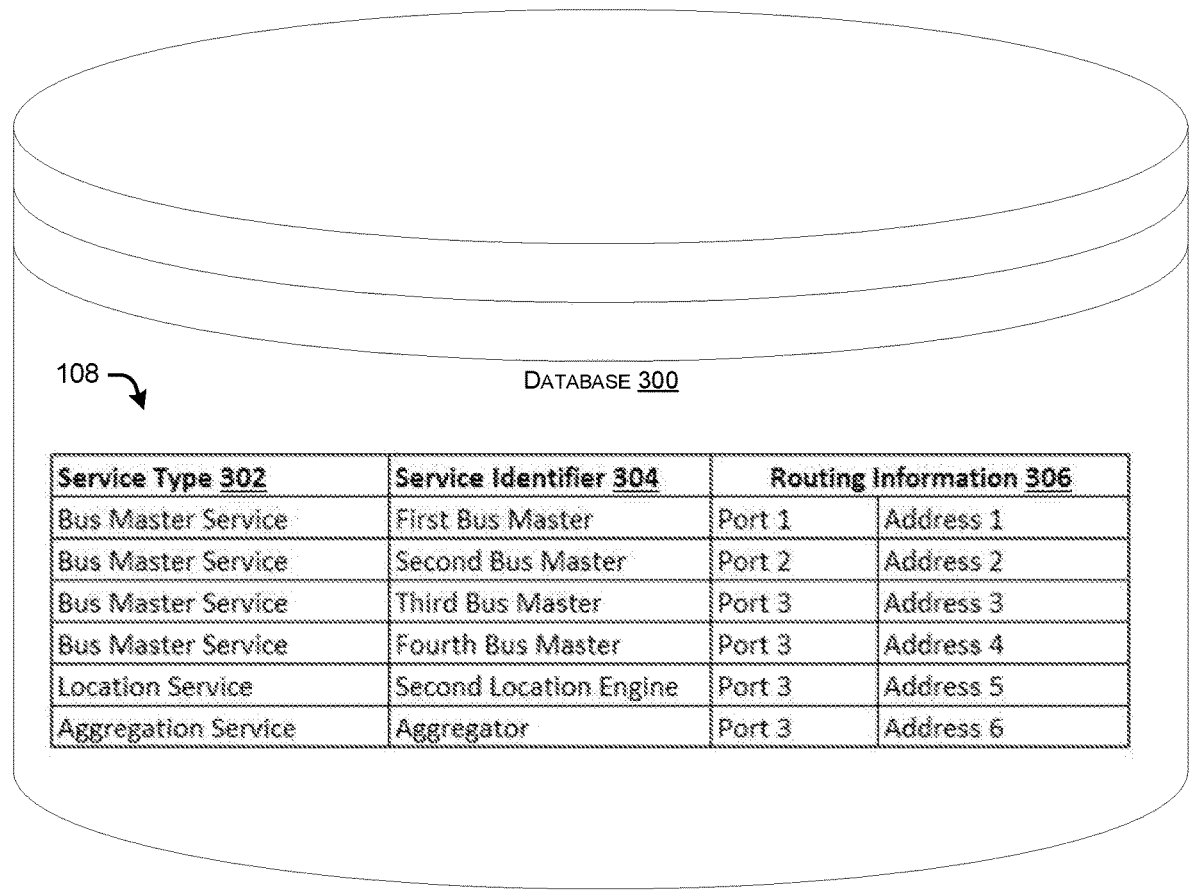
FIG. 3 illustrates a database storing an example of the service list, according to some implementations of the present disclosure.

FIG. 3 illustrates a database 300 storing an example of the service list 108, according to some implementations of the present disclosure. The service list 108 depicted in FIG. 3 may be the service list 108 managed by a mesh module running on the first location engine 110-1, for example. In various implementations, the service list 108 may be stored in local memory of a device implementing the first location engine 110-1.

The service list 108 includes various entries corresponding to various nodes connected to the mesh network. Each of the entries includes at least three fields: a service type field 302, a service identifier field 304, and a routing information field 306. The service type field 302 may identify the type of service provided by the network nodes in the mesh network. For instance, the service type field 302 of an entry may indicate that the network node corresponding to the entry provides a bus master service, a location service, an aggregation service, or the like.

The service identifier field 304 may identify a unique identifier of the service, such as the node that is hosting the service. The unique identifier could be a code that can uniquely identify each network node, such as a proprietary 32-bit code. In some cases, the unique identifier of a node could include at least one of a DNS name of the node, an IP address of the node, a MAC address of the node, or the like.

The routing information field 306 may identify how each node is connected within the mesh network. For instance, as illustrated in FIG. 3, the routing information field 306 could identify port numbers associated with how each node is connected to the network node associated with the database 300. With reference to FIG. 1, the first location engine 110-1 is connected to the first bus master 102-1 via a Port 1, the second bus master 102-2 via a Port 2, and the aggregator 114 via a Port 3. Because the first location engine 110-1 is connected to the second location engine 110-2, the third bus master 102-3, and the fourth bus master 102-4 through the aggregator 114, the service list 108 of the first location engine 110-1 may indicate that the second location engine 110-2, the third bus master 102-3, and the fourth bus master 102-4 are all connected via Port 3. In addition, the routing information field 306 may further include an address for the service itself. For example, the bus master service 106 hosted on the first bus master 102-1 may have a different address than the bus master service hosted on the second bus master 102-2. For instance, each individual service hosted by each individual node in the network may have a unique address (e.g., one of Addresses 1 to 6).

The service list 108 can enable the first location engine 110-1 to track services offered throughout the mesh network. The first location engine 110-1 may access (e.g., subscribe to), or update other nodes about, the services hosted by various nodes in the mesh network. In addition, the first location engine 110-1 can use the service list as a routing table by which to forward messages between nodes and services in the network. For instance, if the first location engine 110-1 receives a message from the first bus master 102-1 addressed to the second location engine 110-2, the first location engine 110-1 may use the service list 108 to identify that the message should be transmitted to the aggregator 114 via Port 3.

Figure 4:
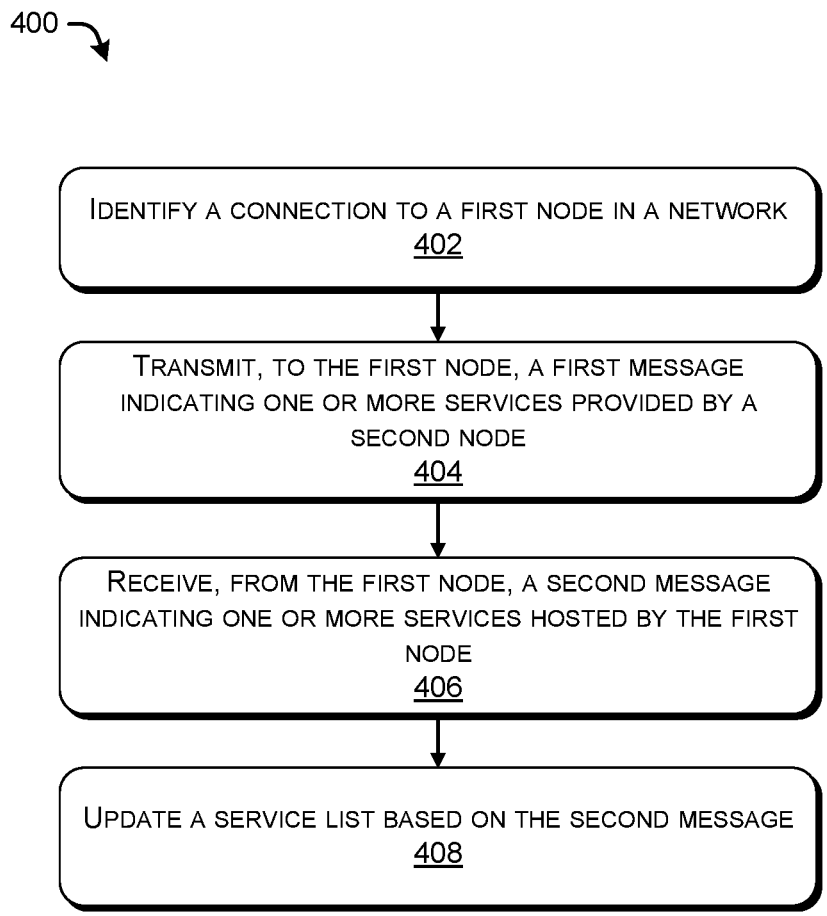
FIG. 4 illustrates an example process for updating a service list in response to connecting to a flexible mesh network.

FIG. 4 illustrates an example process 400 for updating a service list in response to connecting to a flexible mesh network. The process 400 can be performed by a network node, such as any of the bus masters 102, location engines 110, aggregator 114, first node 202, or second node 206 described above with reference to FIGS. 1 to 3.

At 402, the network node may identify that it is has been connected a first node in the mesh network. According to various implementations, the network node may determine that it is connected to a LAN that is connected to the first node. The LAN may be a wired LAN, in some cases. The first node may also be a network node, such as any of the bus masters 102, location engines 110, aggregator 114, first node 202, or second node 206 described above with reference to FIGS. 1 to 3. In some cases, the network node can connect to the first node by exchanging routing information, addresses, and the like. The network node may exchange messages with the first node in a handshake procedure to establish a connection between the network node and the first node through the LAN.

At 404, the network node can transmit, to the first node, a first message indicating one or more services provided by a second node. The second node, in some cases, can be the network node performing the process 400. In some instances, the second node can be a different network node that is connected to the network node performing the process 400. In addition, at 406, the network node may receive, from the first node, a second message indicating one or more services hosted by the first node. The service(s) may include, for example, at least one of a bus master service, a location service, or an aggregation service, a data publication service, a configuration service, an industrial control service, or the like. In various implementations, a service can be provided by a software module, a software object, a VM, an independent device, or the like.

At 408, the network node may update a service list based on the second message. For example, if the second message indicates a single service provided by the first node, the network node may add an entry to the service list that identifies the service, the first node, and/or routing information associated with the connection between the network node and the first node. If the second message indicates multiple services, the network node may add multiple entries corresponding to those services, nodes, and routing information to the service list. Accordingly, the network node may efficiently identify and track which services are hosted by nodes in the mesh network.

Figure 5:
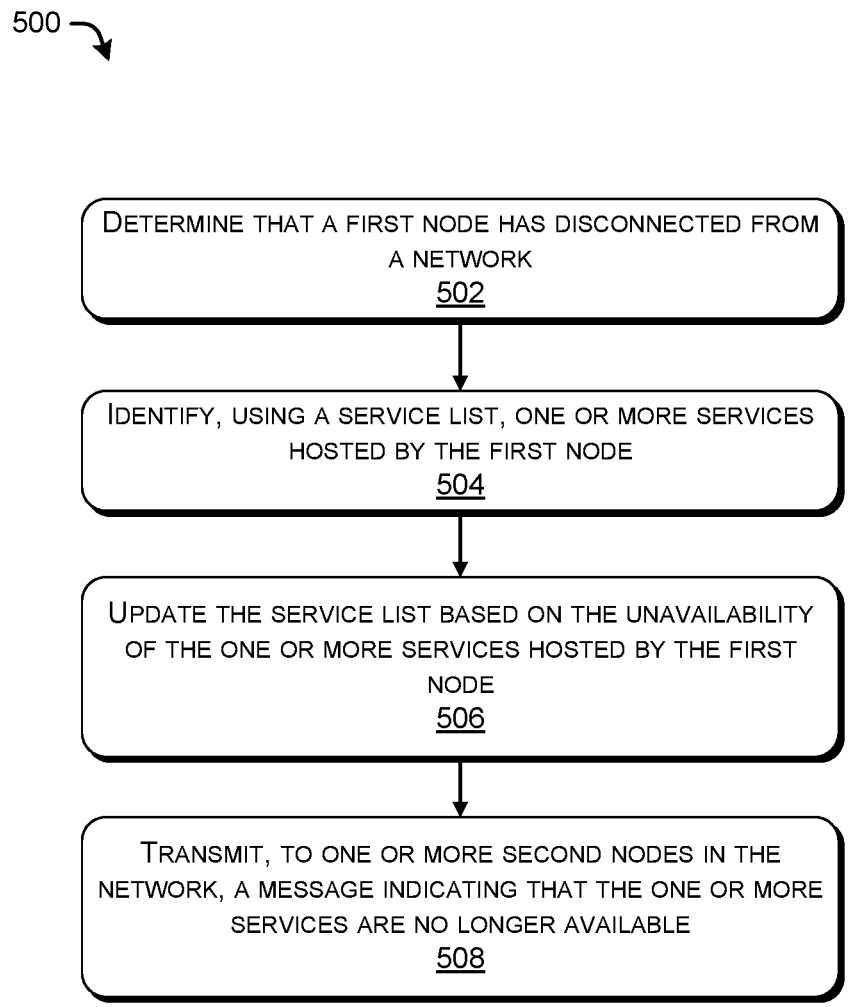
FIG. 5 illustrates an example process for updating nodes in a flexible mesh network regarding a loss of services when one node disconnects from the network.

FIG. 5 illustrates an example process 500 for updating nodes in a flexible mesh network regarding a loss of services when one node disconnects from the network. The process 500 can be performed by a network node, such as any of the bus masters 102, location engines 110, aggregator 114, first node 202, or second node 206 described above with reference to FIGS. 1 to 3.

At 502, the network node may determine that a first node has disconnected from a network. In some cases, the network node may have previously exchanged data with the first node, and may identify that data can no longer be delivered from the first node and/or data has no longer been received from the first node. In various examples, the network node may transmit a ping the first node to determine whether the first node remains connected. For instance, the network node may transmit an Internet Control Message Protocol (ICMP) echo request packet to the first node. If the first node remains connected, the network node may receive an ICMP echo response packet from the first node. If the first node is disconnected, the network node may not receive the ICMP echo response. If the network node determines that the ICMP echo response has not been received in a predetermined time frame (e.g., 50 milliseconds), the network node may determine that the first node has been disconnected.

At 504, the network node may identify, using a service list, one or more services that were hosted by the first node. For example, the service list may include one or more entries corresponding to the service(s) hosted by the first node.

At 506, the network node may update the service list based on the unavailability of the service(s) hosted by the first node. For example, the network node may delete the entries in the service node that correspond to the service(s) hosted by the first node.

At 508, the network node may transmit, to one or more second nodes in the network, a message indicating that the service(s) hosted by the first node are no longer available. In some cases, the network node may transmit the message to one second node that may, in turn, forward the message on to other second nodes in the mesh network. Accordingly, the nodes within the mesh network can be automatically updated when a particular service becomes unavailable within the network.

Figure 6:
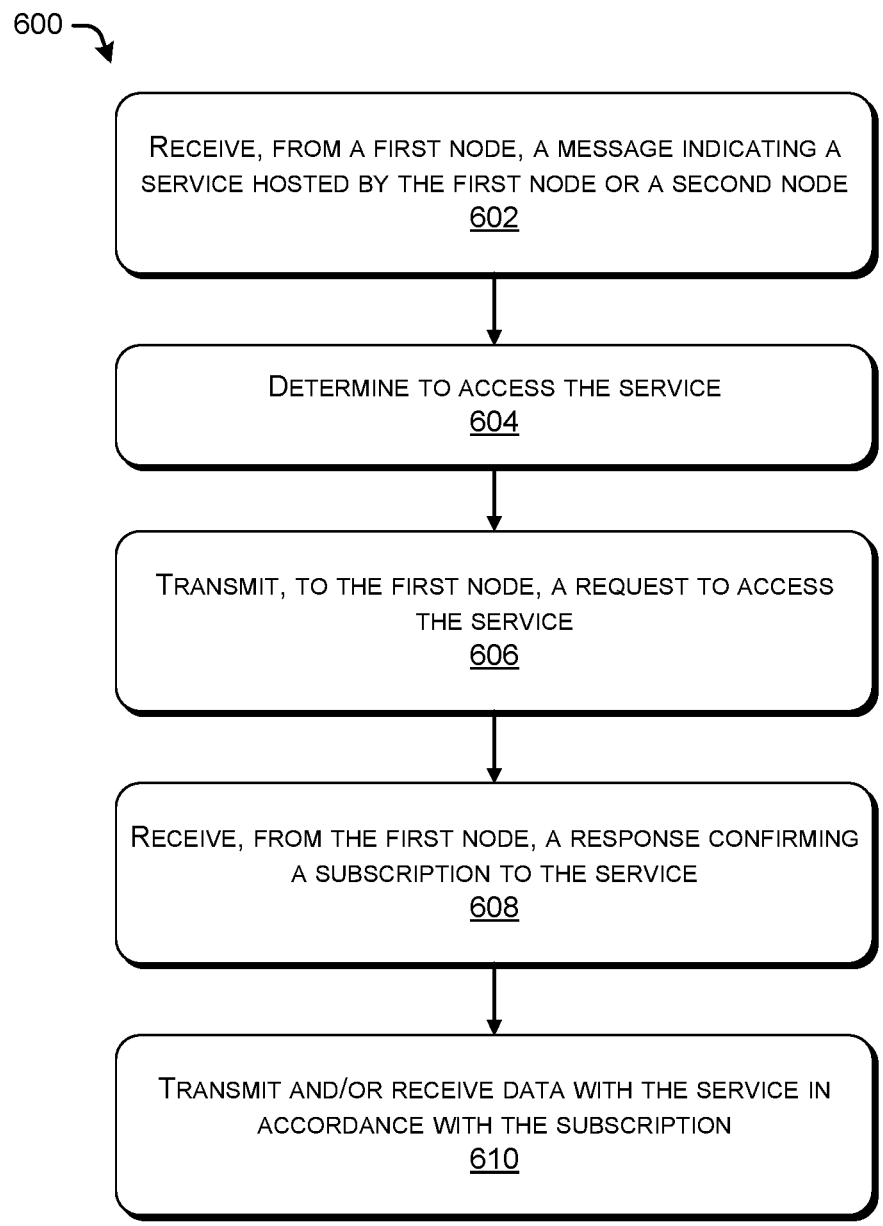
FIG. 6 illustrates an example process for establishing a subscription with a node in a flexible mesh network.

FIG. 6 illustrates an example process 600 for establishing a subscription with a node in a flexible mesh network. The process 500 can be performed by a network node, such as any of the bus masters 102, location engines 110, aggregator 114, first node 202, or second node 206 described above with reference to FIGS. 1 to 3.

At 602, the network node may receive, from a first node, a message indicating a service hosted by the first node or a second node. In some cases, the second node is connected to the first node within the mesh network.

At 604, the network node may determine to access (e.g., subscribe to) the service. For instance, the network node may be configured to automatically access a particular type of service that becomes available within the mesh network. In some examples, an aggregator in a flexible mesh network may be automatically configured to access any location engine that joins the network. In some implementations, the network node may determine to access the service based on input from an external user, such as a system administrator. For example, a system administrator may direct an aggregator in a mesh network to access a bus master service within the network, so that the system administrator can observe an output of the bus master service with location data output by the aggregator.

At 606, the network node transmits, to the first node, a request to access the service. In various implementations, if the service is hosted by the second node, the first node may forward the request to the second node on behalf of the network node. The node hosting the requested service may establish a subscription with the network node. For instance, the node hosting the requested service may identify a socket (e.g., a TCP socket) by which the network node can exchange data with the requested service in accordance with the subscription.

At 608, the network node may receive, from the first node, a response confirming the subscription to the service. In some cases, the response may indicate how the network node can exchange data with the requested service.

At 610, the network node may transmit and/or receive data with the service in accordance with the subscription. Accordingly, the network node may efficiently establish a subscription to a particular service within the mesh network.

Figure 7:
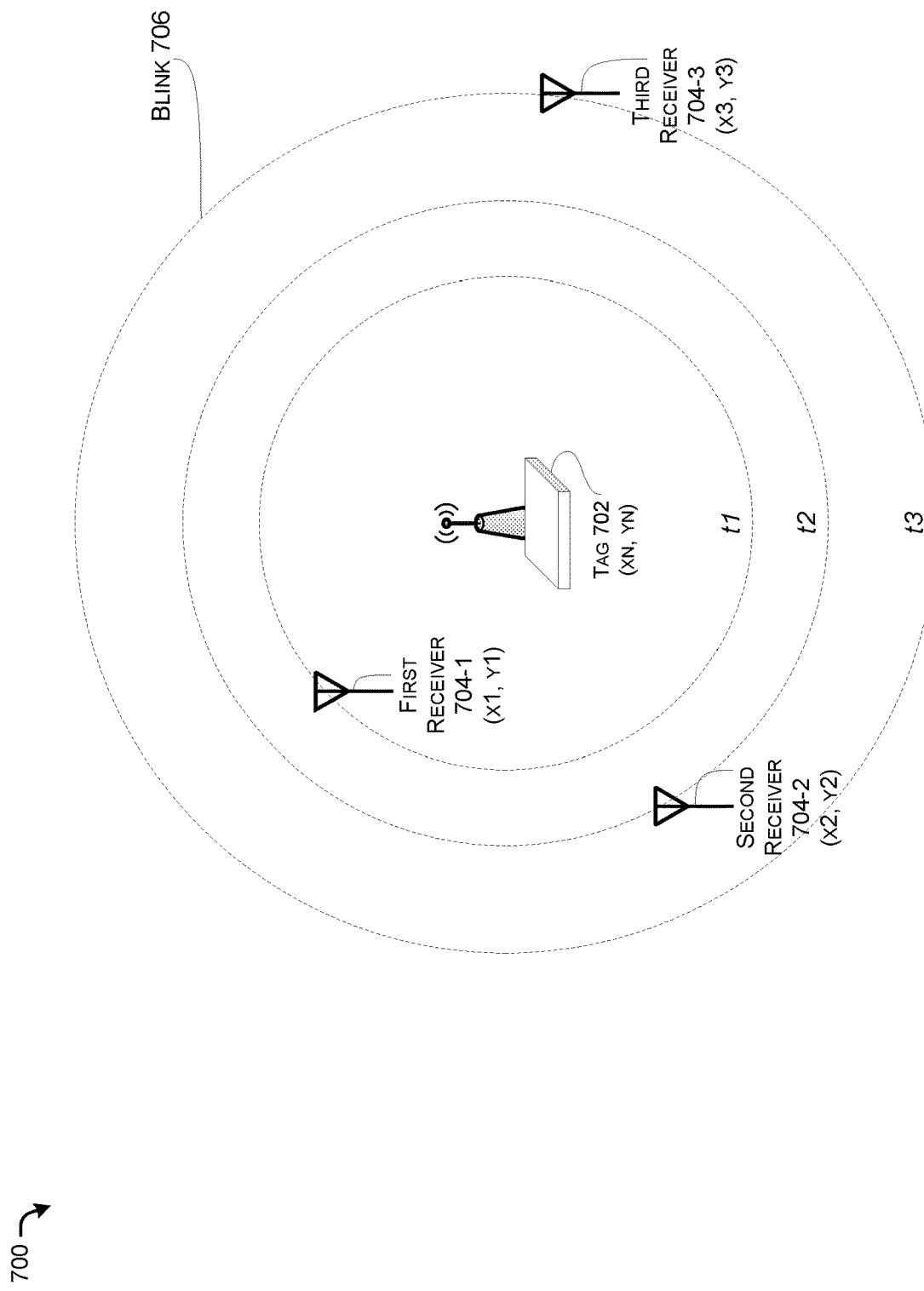
FIG. 7 illustrates an example location system environment.

FIG. 7 illustrates an example location system environment 700. As illustrated, the environment 700 includes a tag 702 and multiple receivers 704-1 to 704-3. In some cases, the environment 700 can correspond to an RTLS.

In various implementations, the tag 702 is configured to broadcast wireless signals. In some cases, the tag 702 may broadcast the wireless signals periodically. For instance, the tag 702 may be configured to broadcast the wireless signals at a frequency of once every five minutes, once a minute, twice a minute, once every ten seconds, once a second, multiple times per second, or the like. According to some examples in which the tag 702 is carried or affixed by a moving object or person, the tag 702 may broadcast the wireless signals at a frequency of once every 10-1000 milliseconds.

In some cases, the tag 702 may broadcast the wireless signals in response to an event. For instance, the tag 702 may broadcast the wireless signals in response to receiving a request for the wireless signals from another device, or in response to some other type of event. The wireless signals can be electromagnetic signals (e.g., infrared signals, radio signals, etc.), ultrasonic signals, subsonic signals, or the like.

The receivers 704-1 to 704-3 may be configured to receive the wireless signals from the tag 702, and to recognize the times at which the wireless signals are received. The receivers 704-1 to 704-3 may be referred to as "anchors" in some cases. In various implementations, the receivers 704-1 to 704-3 are located at known positions. In some implementations, the receivers 704-1 to 704-3 may be mounted at fixed positions on walls, ceilings, or fixtures within a hospital building. The receivers 704-1 to 704-3 may be located at different positions. As illustrated in FIG. 1, a first receiver 704-1 may be located at position ($x_1$, $y_1$), a second receiver 704-2 may be located at position ($x_2$, $y_2$), and a third receiver 704-3 may be located at a position ($x_3$, $y_3$). Although the environment 700 illustrated in FIG. 7 is depicted two dimensions, in some cases, the environment 700 can be defined in three dimensions.

In some cases, the receivers 704-1 to 704-3 may be further configured to communicate with each other over a wired (e.g., ethernet, fiber-optic, etc.) and/or wireless (e.g., Wi-Fi, Bluetooth, etc.) LAN.

In some implementations, a single wireless signal broadcast by the tag 702 may be referred to as a "blink." As depicted in FIG. 1, an example blink 706 is transmitted from the tag 702 at time=$t_0$. The blink 706 is received at the first receiver 704-1 at time=$t_1$, at the second receiver 704-1 at time=$t_2$, and at the third receiver 704-3 at time=$t_3$.

The position of the tag 702 may be derived based on the positions of the receivers 704-1 to 704-3 and the times at which the receivers 704-1 to 704-3 receive the blink 706. In various example implementations, the distances between the tag 702 and the receivers 704-1 to 704-3 may be calculated.

In some cases, the blink 706 indicates to. At least one of the receivers 704-1 to 704-3 may be able to derive to from the blink 706. Accordingly, a time-of-flight of the blink 706 between the tag 702 and each one of the receivers 704-1 to 704-3 can be derived according to the following Formula 1:

$$\Delta t = t_n - t_0 \qquad \text{Formula 1}$$

wherein $\Delta t$ is the time-of-flight of the blink 706, $t_n$ is the time at which a receiver receives the blink 706 (e.g., $t_1$ for the first receiver 704-1, $t_2$ for the second receiver 704-2, and $t_3$ for the third receiver 704-3), and to is the time at which the tag 702 transmits the blink 706.

Based on the times-of-flight of the blink 706 between the tag 702 and the receivers 704-1 to 704-3, distances between the tag 702 and the receivers 704-1 to 704-3 can be derived based on the following Formula 2:

$$d = \Delta t * v \qquad \text{Formula 2}$$

wherein d is the distance between the tag 702 and a particular receiver, $\Delta t$ is the time-of-flight of the blink 706 between the tag 702 and the particular receiver, and v is the velocity of the blink 706. If the blink 706 is an electromagnetic signal, the velocity of the blink 706 can be estimated as the speed of light. If the blink 706 is an ultrasonic or subsonic signal, the velocity of the blink 706 can be estimated as the speed of sound (e.g., through air).

Finally, the position of the tag 702 can be calculated based on the distances between the tag 702 and the receivers 704-1 to 704-3, as well as the known positions of the receivers 704-1 to 704-3. If the position of the tag 702 is defined as ($x_n$, $y_n$), the following Formulas 3 can be used to derive the position of the tag 702:

$$d_1^2 = (x_1 - x_n)^2 + (y_1 - y_n)^2$$

$$d_2^2 = (x_2 - x_n)^2 + (y_2 - y_n)^2$$

$$d_3^2 = (x_3 - x_n)^2 + (y_3 - y_n)^2 \qquad \text{Formulas 3}$$

wherein $d_1$ is the distance between the first receiver 704-1 and the tag 702, $d_2$ is the distance between the second receiver 704-2 and the tag 702, $d_3$ is the distance between the third receiver 704-3 and the tag 702, $x_1$ is the position of the first receiver 704-1 on the x axis, $y_1$ is the position of the first receiver 704-1 on they axis, $x_2$ is the position of the second receiver 704-2 on the x axis, $y_2$ is the position of the second receiver 704-2 on they axis, $x_3$ is the position of the third receiver 704-3 on the x axis, and $y_3$ is the position of the third receiver 704-3 on they axis.

In some implementations, to may be unknown. In these cases, the position of the tag 702 can be derived by solving for $x_n$ and $y_n$ in the following Formulas 4:

$$(v(t_1 - t_0))^2 = (x_1 - x_n)^2 + (y_1 - y_n)^2$$

$$(v(t_2 - t_0))^2 = (x_2 - x_n)^2 + (y_2 - y_n)^2$$

$$(v(t_3 - t_0))^2 = (x_3 - x_n)^2 + (y_3 - y_n)^2 \qquad \text{Formulas 4}$$

wherein $t_1$, is the time at which the first receiver 704-1 receives the blink 706, $t_2$ is the time at which the second receiver 704-2 receives the blink 706, $t_3$ is the time at which the third receiver 704-3 receives the blink 706, to is the time at which the tag 702 transmits the blink 706, $x_1$ is the position of the first receiver 704-1 on the x axis, $y_1$ is the position of the first receiver 704-1 on they axis, $x_2$ is the position of the second receiver 704-2 on the x axis, $y_2$ is the position of the second receiver 704-2 on they axis, $x_3$ is the position of the third receiver 704-3 on the x axis, and $y_3$ is the position of the third receiver 704-3 on they axis. Using Formulas 4 above, the to term can be eliminated and the $x_n$ and $y_n$ terms can be derived.

In some implementations, one of the receivers 704-1 to 704-3 receives timing information from the other receivers. For instance, the first receiver 704-1 may receive a timing report indicating $t_2$ from the second receiver 704-2 and may receive a timing report indicating $t_3$ from the third receiver 704-3. In some cases, the receiver with the timing information calculates the position of the tag 702. In various examples, the receiver with the timing information forwards the timing information to a location system, which can calculate the location of the tag 702 using the timing information.

According to some implementations, individual receivers calculate timing differentials representing the differences between the reception times of different receivers. For instance, upon receiving the blink 706 at $t_1$, the first receiver 704-1 may transmit a synchronization signal to the second receiver 704-2 and the third receiver 704-3. In some cases, the synchronization signal may indicate $t_1$. In some examples in which the synchronization signal is transmitted between the receivers over a high speed (e.g., wired) network, the time at which the synchronization signal is received may be estimated as $t_1$. The second receiver 704-2 may calculate the differential $t_2 - t_1$, and the third receiver 704-3 may calculate the differential $t_3 - t_1$ based on the synchronization signal. The second and third receivers 704-2 and 704-3 may transmit the calculated differentials back to the third receiver 704-1.

Figure 8:
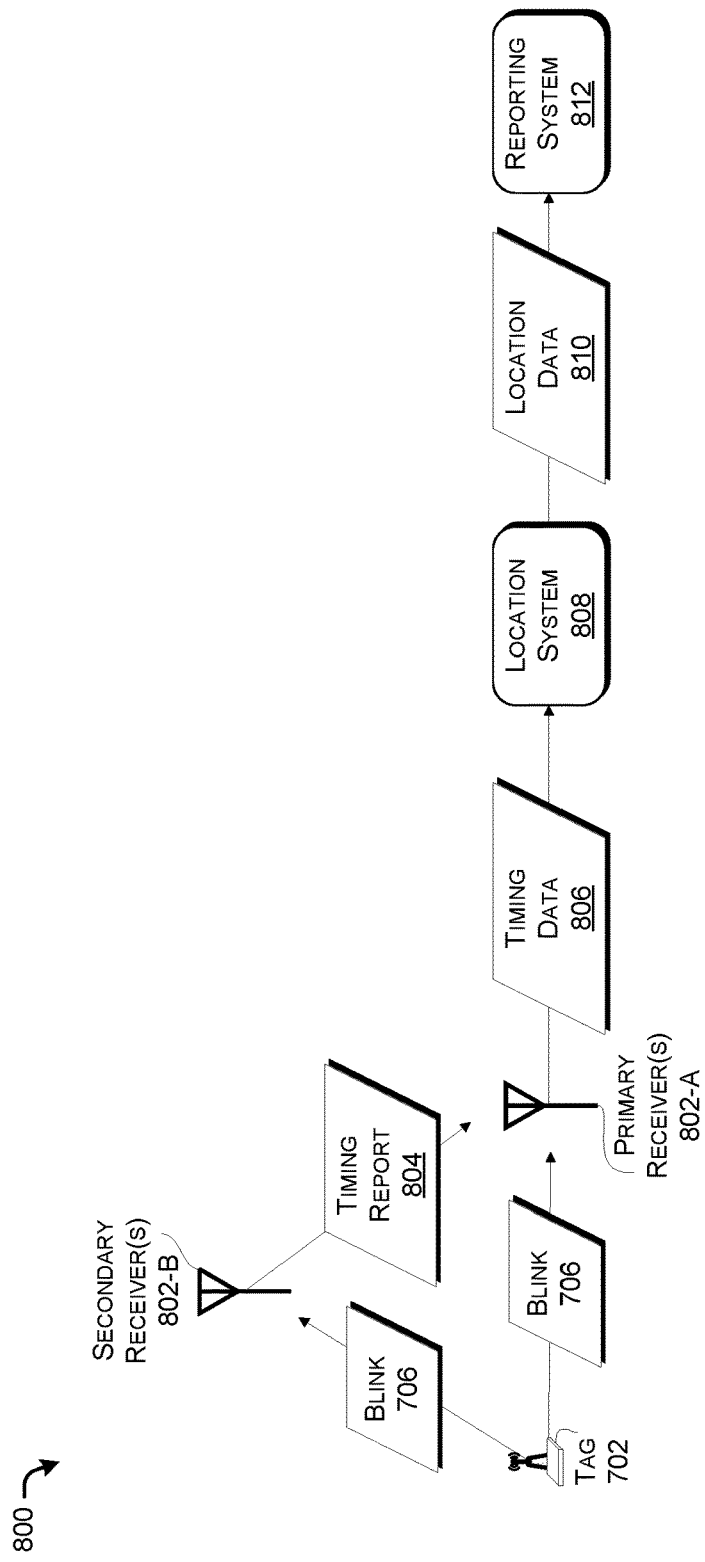
FIG. 8 illustrates an example environment for locating tags in a clinical environment.

FIG. 8 illustrates an example environment 800 for locating tags in a clinical environment. As illustrated, the environment 800 includes the tag 702 transmitting the blink 706, described above with reference to FIG. 7.

As illustrated in FIG. 8, the tag 702 transmits the blink 706 to multiple receivers 802-A and 802-B. In some implementations, the multiple receivers 802-A and 802-B can include the receivers 704-1 to 704-3 described above with reference to FIG. 7. The multiple receivers 802-A and 802-B include primary receiver(s) 802-A and secondary receiver(s) 802-B. The primary receiver(s) 802-A may be connected to the secondary receiver(s) 802-B over a wired and/or wireless LAN. The secondary receiver(s) 802-B may be configured to identify time(s) when the blink 706 is received by the secondary receiver(s) 802-B and may inform the primary receiver(s) 802-A of the time(s) in a timing report 804. The timing report 804 may be transmitted over the LAN. The primary receiver(s) 802-A may be configured to identify time(s) when the blink 706 is received by the primary receiver(s) 802-A, identify time(s) when the blink 706 is received by the secondary receiver(s) 802-B based on the timing report 804, and may aggregate the times in timing data 806. The primary receiver(s) 802-A may transmit the timing data 806 to a location system 808. In some cases, the timing data 806 may indicate identifiers of the primary receiver(s) 802-A and the secondary receiver(s) 802-B along with the receipt times of the blink 706. In some examples, the timing data 806 may indicate the locations of the primary receiver(s) 802-A and the secondary receiver(s) 802-B along with the receipt times of the blink 706.

In various examples, the primary receiver(s) 802-A and/or the secondary receiver(s) 802-B are configured to transmit the timing data 806 to the location system 808. For example, in some cases, the primary receiver(s) 802-A may transmit a synchronization message (e.g., a wireless broadcast signal) indicating at least one time at which the primary receiver(s) 802-A received the blink 706 from the tag 702. The secondary receiver(s) 802-B may receive the synchronization message from the primary receiver(s) 802-A and may generate the timing data 806 to indicate the time(s) at which the primary receiver(s) 802-A received the blink 706 as well as to indicate at least one time at which the secondary receiver(s) 802-B received the blink 706. The secondary receiver(s) 802-B may transmit the timing data 806 to the location system 808.

The location system 808 may be configured to identify the location of the tag 702 based on the timing data 806. In various implementations, the location system 808 can be a computer system including at least one processor configured to perform operations stored in memory. In some cases, the location system 808 may be able to identify the locations of the primary receiver(s) 802-A and the secondary receiver(s) 802-B by cross-refencing identifiers of the primary receiver(s) 802-A and the secondary receiver(s) 802-B in a database. The identifiers of the primary receiver(s) 802-A and the secondary receiver(s) 802-B may be included in the timing data 806. In some cases, the locations of the primary receiver(s) 802-A and the secondary receiver(s) 802-B may be indicated in the timing data 806 itself.

In various implementations, the location system 808 may be configured to identify the locations of multiple tags including the tag 702. To distinguish the timing data 806 associated with the tag 702 from other timing data associated with other tags, the primary receiver(s) 802-A may generate the timing data 806 indicate the identifier of the tag 702. In some examples, the location system 808 comprises the bus masters 102-1 to 102-4, the location engines 110-1 and 110-2, and the aggregator 114 described above with reference to FIG. 1.

Once the location system 808 identifies the location of the tag 702, the location system 808 may indicate the location in location data 810. In some cases, the location data 810 may also indicate the identifier of the tag 702. The location system 808 may transmit the location data 810 to a reporting system 812. The reporting system 812 may output the location of the tag 702 and/or take various other actions based on the location of the tag 702. For instance, if the tag 702 is associated with a care provider and the reporting system 812 determines that the tag 702 is located within the vicinity of a patient in need of immediate care, the reporting system 812 may selectively notify the care provider of the patient's need and request that the care provider attend to the patient.

In various implementations, at least one of the location system 808 and the reporting system 812 may be located outside of an internal network within the clinical environment. At least one firewall may be disposed between the primary receiver(s) 802-A and the location system 808, within the location system 808, between the location system 808 and the reporting system 812, or within the reporting system 812. Accordingly, a security policy within the clinical environment can be enforced.

Figure 9:
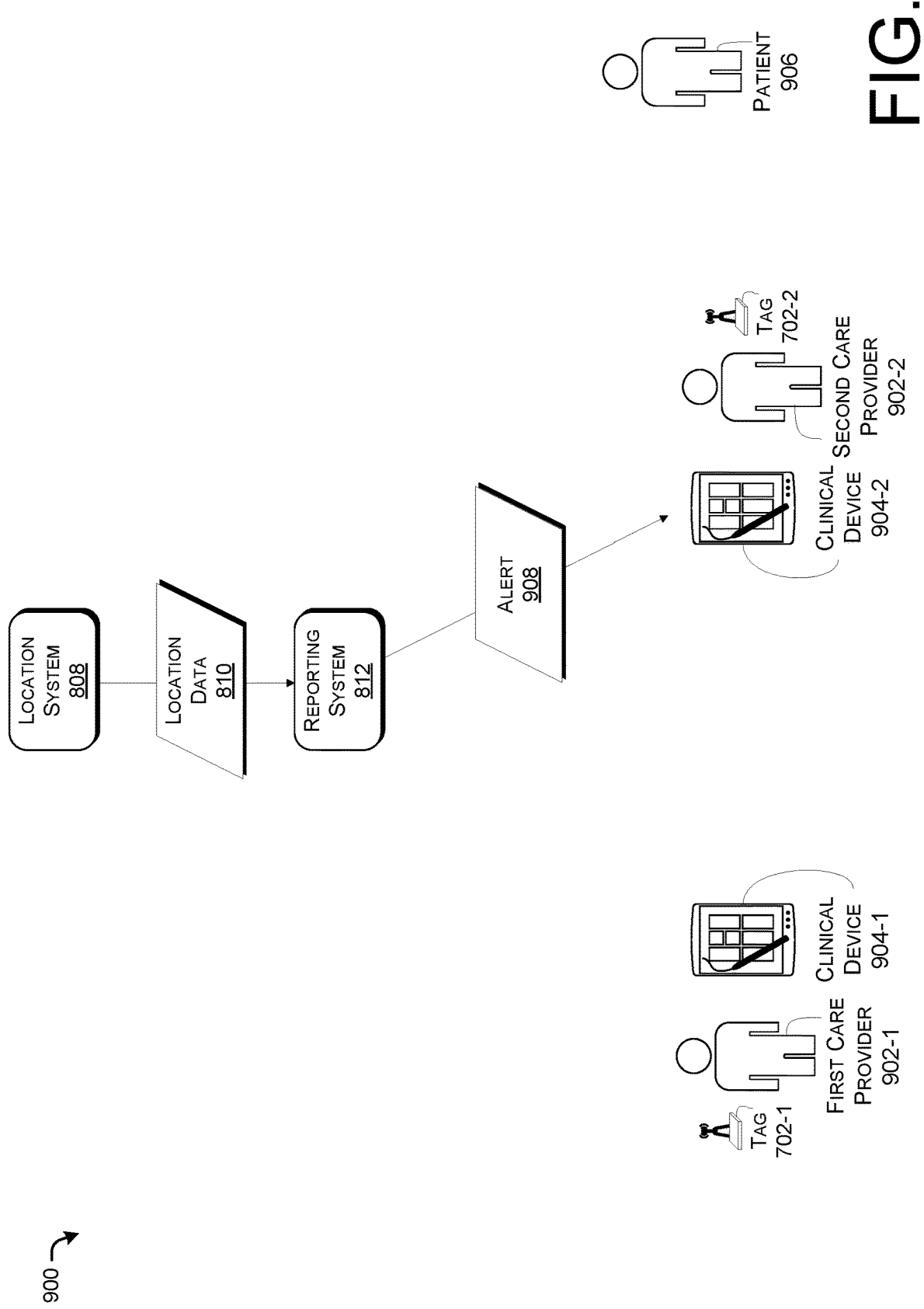
FIG. 9 illustrates an example environment of a location system being utilized in a clinical environment.

FIG. 9 illustrates an example environment 900 of a location system 808 being utilized in a clinical environment. As noted above, the location system 808 may provide the reporting system 812 with the location data 810. The location data 810 may indicate the locations of various tags (e.g., tag 702) throughout the clinical environment. In the example illustrated in FIG. 9, the location data 810 may indicate the locations of first and second tags 702-1 and 702-2 in the clinical environment.

First tag 702-1 may be worn by, held by, or attached to a first care provider 902-1. The first care provider 902-1 may be associated with a first clinical device 904-1. The first clinical device 904-1 may be a mobile device, in some cases. In various implementations, the first clinical device 904-1 could output alerts, instructions, or the like, to assist the first care provider 902-1 with treating and monitoring patients within the clinical environment. For example, the first clinical device 904-1 may be a tablet computer, a laptop computer, a desktop computer, a mobile phone, or the like.

Similarly, second tag 702-2 may be worn by, held by, or attached to a second care provider 902-2. The second care provider 902-2 may be associated with a second clinical device 904-2. The second clinical device 904-2 may be a mobile device, in some cases. In various implementations, the second clinical device 904-2 could output alerts, instructions, or the like, to assist the second care provider 902-2 with treating and monitoring patients within the clinical environment. For example, the second clinical device 904-2 may be a tablet computer, a laptop computer, a desktop computer, a mobile phone, or the like In various implementations, the reporting system 812 may identify that a patient 906 is in need of assistance from a care provider, such as either one of the care providers 902-1 or 902-2. For example, the reporting system 812 may identify that the patient 906 is in need of non-emergency care (e.g., changing of a wound dressing, drug administration, or the like) or emergency care (e.g., defibrillation, tracheostomy, or the like). The reporting system 812 may also be aware of the location of the patient 906.

In some instances, the reporting system 812 may compare the location data 810 to the location of the patient to identify which one of the tags 702-1 or 702-2 is closest to the patient 906. The reporting system 812 may determine that the second tag 702-2 is located closer to the patient 906 than the first tag 702-1. Based on this comparison, the reporting system 812 may identify that the second tag 702-2 is closest to the patient 906.

The reporting system 812 may identify that the tag 702-2 is associated with the second care provider 902-2 and/or the clinical device 904-2 utilized by the second care provider 902-2. The reporting system 812 can selectively transmit an alert 908 to the second clinical device 904-2. In response to receiving the alert, the second clinical device 904-2 may output, to the second care provider 902-2, an instruction to provide assistance to the patient 906.

Figure 10:
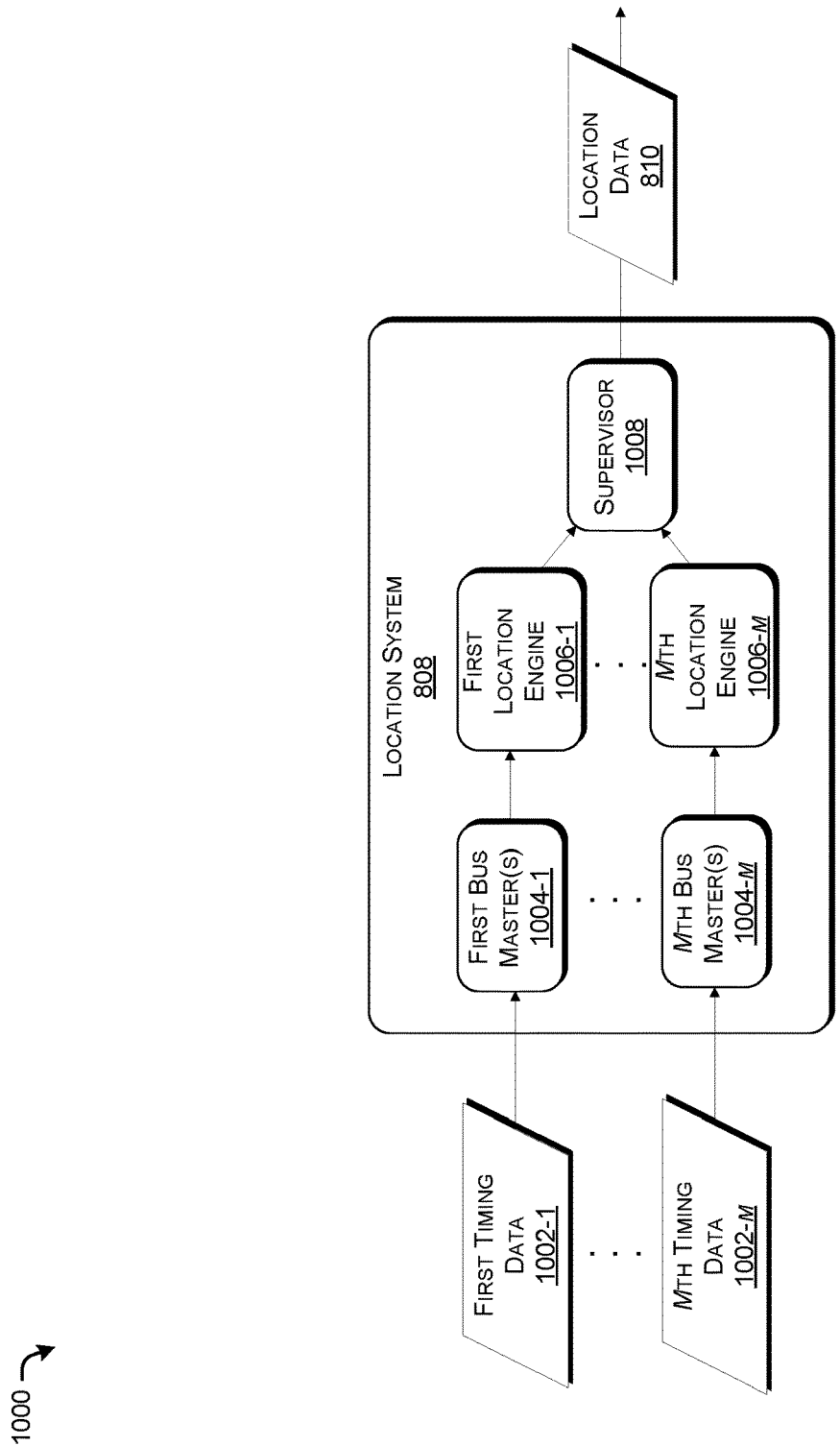
FIG. 10 illustrates an example environment for determining the locations of multiple tags in a clinical environment.

FIG. 10 illustrates an example environment 1000 for determining the locations of multiple tags in a clinical environment. As illustrated, the environment 1000 includes the location system 808 and the location data 810 described above with reference to FIG. 8.

First through mth timing data 1002-1 to 1002-$m$ may be received at first to mth bus masters 1004-1 to 1004-$m$ in the location system 808. The timing data 1002-1 to 1002-$m$ may represent timing data from multiple receivers receiving signals from multiple tags in the clinical environment. For instance, first timing data 1002-1 may represent timing data from multiple primary receivers based on blinks from multiple tags. In some cases, the timing data 1002-1 to 1002-$m$ can be represented in data streams transferred from the primary receivers to the first to mth bus masters 1004-1 to 1004-$m$.

The bus masters 1004-1 to 1004-$m$ may each include hardware and/or software including a serial connection to which multiple receivers (e.g., multiple primary receivers) are connected. In various implementations, the bus masters 1004-1 to 1004-$m$ may be configured to orchestrate communications between the multiple receivers and other network nodes within the location system 806. In some cases, the bus masters 1004-1 to 1004-$m$ are connected to other network nodes within the location system 806 via a LAN.

In some cases, the bus masters 1004-1 to 1004-$m$ may generate individual data packets associated with single blink events (e.g., the same blink from the same tag) and transmit the individual data packets to the location engines 1006-1 to 1006-$m$. When the bus masters 1004-1 to 1004-$m$ receive timing data 1002-1 to 1002-$m$ from multiple primary receivers based on the same blink event, the bus masters 1004-1 to 1004-$m$ may be able to aggregate the subset of the timing data 1002-1 to 1002-$m$ from the same blink event into individual data packets.

The locating engines 1006-1 to 1006-$p$ may be configured to calculate the locations of the tags based on the data received from the bus masters 1004-1 to 1004-$m$. In some cases, p<m, such that there is a greater number of bus masters 1004-1 to 1004-$m$ than locating engines 1006-1 to 1006-$p$. For instance, multiple bus masters 1004-1 to 1004-$m$ may be connected to a single one of the locating engines 1006-1 to 1006-$p$.

A single supervisor (also referred to as an "aggregator") 708 may receive indications of the calculated locations from the location engines 1006-1 to 1006-$p$. The single supervisor 1008 may aggregate the locations into location data 810. The location data 810 may be in the form of a data stream indicating individual tags and their calculated locations. Each one of the bus masters 1004-1 to 1004-$m$, locating engines 1006-1 to 1006-$p$, and aggregator 708 may be network nodes.

Figure 11:
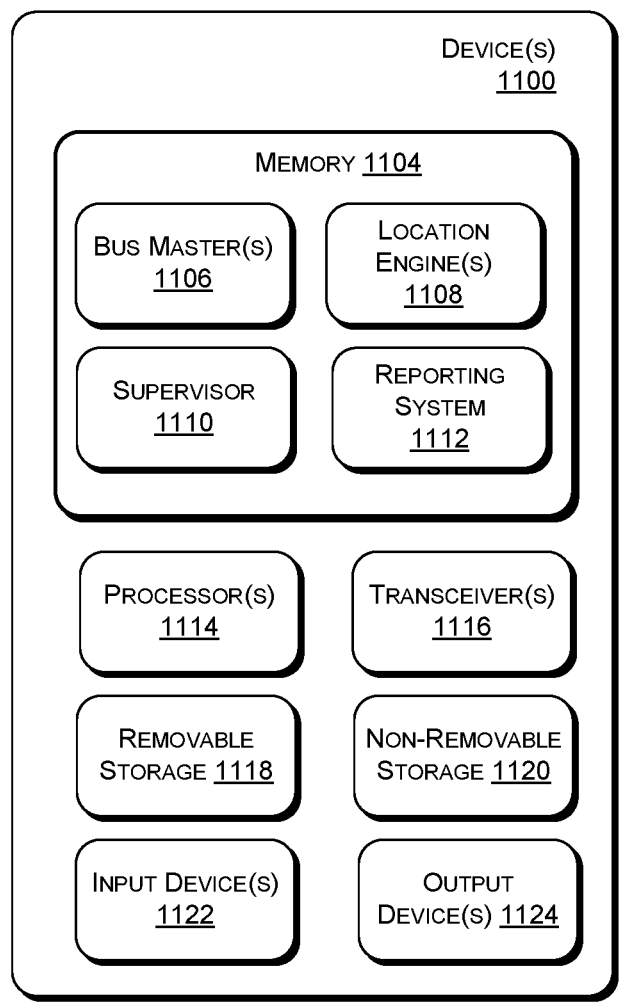
FIG. 11 illustrates at least one example device configured to enable and/or perform the some or all of the functionality discussed herein.

FIG. 11 illustrates at least one example device 1100 configured to enable and/or perform the some or all of the functionality discussed herein. Further, the device(s) 1100 can be implemented as one or more server computers 1102, a network element on a dedicated hardware, as a software instance running on a dedicated hardware, or as a virtualized function instantiated on an appropriate platform, such as a cloud infrastructure, and the like. It is to be understood in the context of this disclosure that the device(s) 1100 can be implemented as a single device or as a plurality of devices with components and data distributed among them.

As illustrated, the device(s) 1100 comprise a memory 1104. In various embodiments, the memory 1104 is volatile (including a component such as Random Access Memory (RAM)), non-volatile (including a component such as Read Only Memory (ROM), flash memory, etc.) or some combination of the two.

The memory 1104 may include various components, such as at least one bus master 1106, at least one location engine 1108, a supervisor 1110, a reporting system 1112, and the like. Any of the bus master(s) 1106, the location engine(s) 1108, the supervisor 1110, and the reporting system 1112 can comprise methods, threads, processes, applications, or any other sort of executable instructions. The bus master(s) 1106, the location engine(s) 1108, the supervisor 1110, and the reporting system 1112 and various other elements stored in the memory 1104 can also include files and databases.

The memory 1104 may include various instructions (e.g., instructions in the bus master(s) 1106, location engine(s) 1108, supervisor 1110, and/or reporting system 1112), which can be executed by at least one processor 1114 to perform operations. In some embodiments, the processor(s) 1114 includes a Central Processing Unit (CPU), a Graphics Processing Unit (GPU), or both CPU and GPU, or other processing unit or component known in the art.

The device(s) 1100 can also include additional data storage devices (removable and/or non-removable) such as, for example, magnetic disks, optical disks, or tape. Such additional storage is illustrated in FIG. 11 by removable storage 1118 and non-removable storage 1120. Tangible computer-readable media can include volatile and nonvolatile, removable and non-removable media implemented in any method or technology for storage of information, such as computer readable instructions, data structures, program modules, or other data. The memory 1104, removable storage 1118, and non-removable storage 1120 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 1100. Any such tangible computer-readable media can be part of the device(s) 1100.

The device(s) 1100 also can include input device(s) 1122, such as a keypad, a cursor control, a touch-sensitive display, voice input device, etc., and output device(s) 1124 such as a display, speakers, printers, etc. These devices are well known in the art and need not be discussed at length here. In particular implementations, a user can provide input to the device(s) 500 via a user interface associated with the input device(s) 1122 and/or the output device(s) 1124.

As illustrated in FIG. 11, the device(s) 1100 can also include one or more wired or wireless transceiver(s) 1116. For example, the transceiver(s) 1116 can include a Network Interface Card (NIC), a network adapter, a LAN adapter, or a physical, virtual, or logical address to connect to the various base stations or networks contemplated herein, for example, or the various user devices and servers. To increase throughput when exchanging wireless data, the transceiver(s) 1116 can utilize Multiple-Input/Multiple-Output (MIMO) technology. The transceiver(s) 1116 can include any sort of wireless transceivers capable of engaging in wireless, Radio Frequency (RF) communication. The transceiver(s) 1116 can also include other wireless modems, such as a modem for engaging in Wi-Fi, WiMAX, Bluetooth, or infrared communication.

In some implementations, the transceiver(s) 1116 can be used to communicate between various functions, components, modules, or the like, that are comprised in the device(s) 1100. For instance, the transceivers 1116 may facilitate communications between the bus master(s) 1106, the location engine(s) 1108, the supervisor 1110, and/or the reporting system 1112.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

The invention claimed is:

1. A location engine, comprising:
   at least one processor; and
   memory storing instructions that, when executed by the at least one processor, cause the at least one processor to perform operations comprising:
   connecting to an aggregator in a mesh network;
   transmitting, to the aggregator, a first message indicating a location service hosted by the location engine and a bus master service hosted by a bus master;
   receiving, from the aggregator, a second message indicating an aggregation service hosted by the aggregator;
   storing, in a service list, an entry corresponding to the aggregation service hosted by the aggregator;
   transmitting, to the aggregator, a request to access the aggregation service;
   receiving, from the aggregator, a response confirming a subscription to the aggregation service;
   receiving, from the bus master, a single data stream indicating times at which multiple receivers in a clinical environment received a wireless signal from a tag;
   identifying a location of the tag in the clinical environment based on the single data stream; and
   transmitting, to the aggregator, the location of the tag in accordance with the subscription.

2. The location engine of claim 1, wherein the request is a first request, the response is a first response, and the subscription is a first subscription, the operations further comprising: receiving, from the aggregator, a second request to access the bus master service hosted by the bus master; transmitting, to the bus master, the second request; receiving, from the bus master, a second response confirming a second subscription of the aggregator to the bus master service; transmitting, to the aggregator, the second response; and forwarding the single data stream to the aggregator.

3. The location engine of claim 2, wherein the entry is a first entry that identifies a first port associated with the aggregator, the operations further comprising: storing, in the service list, a second entry corresponding to the bus master service hosted by the bus master, the second entry identifying a first port associated with the bus master; in response to receiving the second request, identifying the first port corresponding to the bus master using the second entry; and in response to receiving the second response, identifying the second port corresponding to the aggregator using the first entry.

4. The location engine of claim 1, wherein the location engine is a first location engine, and the location service is first location service, and the entry is a first entry, the operations further comprising: receiving, from the aggregator, a third message indicating a second location service hosted by a second location engine that is connected to the aggregator; and storing, in the service list, a second entry corresponding to the second location service hosted by the second location engine.

5. The first location engine of claim 4, wherein the bus master is a first bus master and the bus master service is a first bus master service, the operations further comprising: receiving, from the aggregator, a fourth message indicating a second bus master service hosted by a second bus master that is connected to the second location engine; and storing, in the service list, a third entry corresponding to the second bus master service hosted by the second bus master.

6. The first location engine of claim 4, wherein the request is a first request, the response is a first response, the subscription is a first subscription, the single data stream is a first single data stream, the multiple receivers are first multiple receivers, the wireless signal is a first wireless signal, the tag is a first tag, and the location is a first location, the operations further comprising: transmitting, to the second bus master through the aggregator and the second location engine, a second request to access the second bus master service; receiving, from the second bus master through the aggregator and the second location engine, a second response confirming a second subscription to the second bus master service; receiving, from the second bus master through the aggregator and the second location engine, a second single data stream indicating times at which second multiple receivers in a clinical environment received a second wireless signal from a second tag; identifying a second location of the second tag in the clinical environment based on the second single data stream; and transmitting, to the aggregator, the second location of the second tag in accordance with the first subscription.

7. The first location engine of claim 4, wherein the operations further comprise: receiving, from the aggregator, a fourth message indicating that the second location service hosted by the second location engine is no longer available; and in response to receiving the fourth message, deleting the second entry in the service list.

8. The first location engine of claim 1, wherein the entry is a first entry, the operations further comprising: identifying that the bus master has disconnected from the first location engine; in response to identifying that the bus master has disconnected: deleting, in the service list, a second entry corresponding to the bus master service hosted by the bus master; and transmitting, to the aggregator, a third message indicating that the bus master service hosted by the bus master is no longer available.

9. A method performed by a location engine, the method comprising:
   connecting to an aggregator in a mesh network;
   transmitting, to the aggregator, a first message indicating a location service hosted by the location engine and a bus master service hosted by a bus master;

receiving, from the aggregator, a second message indicating an aggregation service hosted by the aggregator;

storing, in a service list, an entry corresponding to the aggregation service hosted by the aggregator;

transmitting, to the aggregator, a request to access the aggregation service;

receiving, from the aggregator, a response confirming a subscription to the aggregation service;

receiving, from the bus master, a single data stream indicating times at which multiple receivers in a clinical environment received a wireless signal from a tag;

identifying a location of the tag in the clinical environment based on the single data stream; and transmitting, to the aggregator, the location of the tag in accordance with the subscription.

10. The method of claim 9, wherein the request is a first request, the response is a first response, and the subscription is a first subscription, the method further comprising:

receiving, from the aggregator, a second request to access the bus master service hosted by the bus master;

transmitting, to the bus master, the second request;

receiving, from the bus master, a second response confirming a second subscription of the aggregator to the bus master service;

transmitting, to the aggregator, the second response; and forwarding the single data stream to the aggregator.

11. The method of claim 10, wherein the entry is a first entry that identifies a first port associated with the aggregator, the method further comprising:

storing, in the service list, a second entry corresponding to the bus master service hosted by the bus master, the second entry identifying a first port associated with the bus master;

in response to receiving the second request, identifying the first port corresponding to the bus master using the second entry; and in response to receiving the second response, identifying the second port corresponding to the aggregator using the first entry.

12. The method of claim 9, wherein the location engine is a first location engine, and the location service is first location service, and the entry is a first entry, the method further comprising:

receiving, from the aggregator, a third message indicating a second location service hosted by a second location engine that is connected to the aggregator; and storing, in the service list, a second entry corresponding to the second location service hosted by the second location engine.

13. The method of claim 12, wherein the bus master is a first bus master and the bus master service is a first bus master service, the method further comprising:

receiving, from the aggregator, a fourth message indicating a second bus master service hosted by a second bus master that is connected to the second location engine; and storing, in the service list, a third entry corresponding to the second bus master service hosted by the second bus master.

14. The method of claim 12, wherein the request is a first request, the response is a first response, the subscription is a first subscription, the single data stream is a first single data stream, the multiple receivers are first multiple receivers, the wireless signal is a first wireless signal, the tag is a first tag, and the location is a first location, the method further comprising:

transmitting, to the second bus master through the aggregator and the second location engine, a second request to access the second bus master service;

receiving, from the second bus master through the aggregator and the second location engine, a second response confirming a second subscription to the second bus master service;

receiving, from the second bus master through the aggregator and the second location engine, a second single data stream indicating times at which second multiple receivers in a clinical environment received a second wireless signal from a second tag;

identifying a second location of the second tag in the clinical environment based on the second single data stream; and transmitting, to the aggregator, the second location of the second tag in accordance with the first subscription.

15. The method of claim 12, further comprising:

receiving, from the aggregator, a fourth message indicating that the second location service hosted by the second location engine is no longer available; and in response to receiving the fourth message, deleting the second entry in the service list.

16. The method of claim 9, wherein the entry is a first entry, the method further comprising:

identifying that the bus master has disconnected from the first location engine;

in response to identifying that the bus master has disconnected:

deleting, in the service list, a second entry corresponding to the bus master service hosted by the bus master; and transmitting, to the aggregator, a third message indicating that the bus master service hosted by the bus master is no longer available.

* * * * *